(12) United States Patent
Bordoni et al.

(10) Patent No.: US 7,723,105 B2
(45) Date of Patent: May 25, 2010

(54) CONDITIONED CELL CULTURE MEDIUM, METHOD TO OBTAIN THE SAME AND USE OF IT FOR MAINTENANCE, PROLIFERATION AND DIFFERENTIATION OF MAMMALIAN CELLS

(75) Inventors: Veronica Bordoni, Rome (IT); Tonino Alonzi, Rome (IT); Marco Tripodi, Rome (IT)

(73) Assignee: Instituto Nazionale per le Malattie, Rome (IT)

( * ) Notice: Subject to any disclaimer, the term of this patent is extended or adjusted under 35 U.S.C. 154(b) by 548 days.

(21) Appl. No.: 10/568,194

(22) PCT Filed: Aug. 10, 2004

(86) PCT No.: PCT/EP2004/051758

§ 371 (c)(1),
(2), (4) Date: Feb. 10, 2006

(87) PCT Pub. No.: WO2005/014799

PCT Pub. Date: Feb. 17, 2005

(65) Prior Publication Data

US 2006/0286081 A1 Dec. 21, 2006

(30) Foreign Application Priority Data

Dec. 8, 2003 (IT) .................. RM2003A0395

(51) Int. Cl.
*C12N 5/00* (2006.01)
*A01N 65/00* (2006.01)
*C12N 5/02* (2006.01)

(52) U.S. Cl. ............... 435/325; 424/93.7; 435/404; 435/405

(58) Field of Classification Search ............... None
See application file for complete search history.

(56) References Cited

U.S. PATENT DOCUMENTS 5,521,076 A * 5/1996 Mulligan et al. ............ 435/456
6,284,236 B1 * 9/2001 Wiley et al. ................. 424/85.1
7,118,746 B1 * 10/2006 Naughton et al. ........... 424/184.1

FOREIGN PATENT DOCUMENTS

WO    WO 2004/016777    2/2004

OTHER PUBLICATIONS

Charbord, P., et al. "Comparative Study of Stromal Cell Lines Derived from Embryonic, Fetal, and Post-Natal Mouse Blood-Forming Tissues" Exper. Hemat. 2002, 30(10), 1202-1210. (Science Direct Abstract Only, 2 pages).*
Bellovino, D., et al. "MMH Cells: An in vitro Model for the Study of Retinol-Binding Protein Secretion Regulated by Retinol" J. Cell. Phys. 1999, 181(1), 24-32. (Wiley-Interscience Abstract Only, 3 pages).*
Napolitano, M., et al. "Oxidation Affects the Regulation of Hepatic Lipid Synthesis by Chylomicron Remnants" Free Radic. Biol. Med. 2001, 30(5) 506-515. (PubMed Abstract Only, 1 page).*
Allen, K., et al. "Conditionally Immortalized Mouse Hepatocytes for Use in Liver Gene Therapy", J.Gastroent.Hepatol. 15(11), 1325-1332. (Blackwell Synergy Abstract Only, 2 pages).*
Barbanti-Brodano, G., et al. "Simian Virus 40 INfection in Humans and Associatino with Human Diseases: Results and Hypotheses" Virology. 2004, 318(1), 1-9. (PubMed Abstract Only, 2 pages).*
Krause, P., et al. "Hepatocyte-Supported Serum-Free Culturtte of Rat Lliver Sinusoidal Endothelial Cells" J. Hepatol. 2000, 32(5) 718-726. (PubMed Abstract Only, 1 page).*
Becton Dickinson (BD) Biosciences, "BD PRIMARIA™ Cultureware", Becton, Dickinson, and Company, <https://www.bdis.com/discovery_labware/ products/display_product. php?keyID=193>, 2007 (accessed online Apr. 16, 2008), 2 pages.*
Alessandro Aiuti et al., "Hematopoietic Support and Cytokine Expression of Murine-Stable Hepatocyte Cell Lines (MMH)", Hepatology 1998, pp. 1645-1654.

(Continued)

*Primary Examiner*—Christopher R Tate
*Assistant Examiner*—Aaron J Kosar
(74) *Attorney, Agent, or Firm*—Stetina Brunda Garred & Brucker

(57) ABSTRACT

The invention relates to a conditioned cell culture medium and a corresponding method to obtain it. The invention also refers to methods of using this cellconditioned medium for the maintenance, proliferation and differentiation of mammalian cells. The culture medium produced in accordance with the present invention is conditioned by the cell secretion activity of murine cells, in particular, those differentiated and immortalized transgenic hepatocytes, named MMH (Met Murine Hepatocyte). These media are employed in in vitro cell culture systems to induce maintenance, proliferation and differentiation of mammalian cells. The cells named MMH are differentiated non transformed murine hepatocytes that produce important biological molecules (e.g cytokines and growth factors) and, in accordance with the present invention, they are used in in vitro cell culture systems for the maintenance, proliferation and differentiation of mammalian cells.

1 Claim, 1 Drawing Sheet

OTHER PUBLICATIONS

Laura Amicone et al., "Transgenic Expression in the Liver of Truncated Met Blocks Apoptosis and Permits Immortalization of Hepatocytes", The EMBO Journal, 1997, pp. 495-503, vol. 16, No. 3.

Veronica Bordoni et al., "Murine Heptocyte Cell Lines Promote Expansion and Differentiation of NK Cells from Stem Cell Precursors", Hepatology, Jun. 2004, pp. 1508-1516, vol. 39, No. 6.

Ellen Kittler, et al; "Biologic Significance of Constitutive and Subliminal Growth Factor Production by Bone Marrow Stroma"; Blood; Jun. 15, 1992; pp. 3168-3178; vol. 79, No. 12.

Connie Evans et al.; "Mechanisms That Regulate the Cell Cycle Status of Very Primitive Hematoietic Cells in Long-Term Human Marrow Cultures. II. Analysis of Positive and Negative Regulators Produced by Stromal Cells Within the Adherent Layer"; Blood; Jul. 1, 1991; pp. 110-117; vol. 78, No. 1.

P.H. Krebsbach et al; "Bone Marrow Stromal Cells: Characterization and Clinical Application"; Crit. Rev. Oral Biol Med.; 1999, 10 (2), pp. 165-181.

Francesca Spagnoli et al.; "Identification of Bipotential Precursor Cell in Hepatic Cell Lines Derived from Transgenic Mice Expressing Syto-Met in the Liver"; The Journal of Cell Biology; Nov. 16, 1998; pp. 1101-1112; vol. 143, No. 4.

Francesca Spagnoli et al.; "Inhibition of MMH (Met Murine Hepatocyte) Cell Differentiation by TGF is Abrogated by Pre-Treatment with Heritable Differentiation Effector FGF1"; Journal of Cell Science; 2000, vol. 143, pp. 3639-3647.

Valerie Pasquetto et al.; "Cytokine-Sensitive Replication of Hepatitis B Virus in Immortalized Mouse Hepatocyte Cultures"; Journal of Virology; Jun. 2000; pp. 5646-5653; vol. 76, No. 11.

David Penington; "Megakaryocyte Colony Culture Using a Liver Cell Conditioned Medium"; Blood Cells; 1979, vol. 5 , pp. 13-23.

Franziska Boess et al.; "Gene Expression in Two Hepatic Cell Lines, Cultured Primary Hepatocytes, and Liver Slices Compared to the In Vitro Liver Gene Expression in Rats: Possible Implications for Toxicogenomics Use of in In Vitro Systems"; Toxicological Sciences; 2003, vol. 73, pp. 386-402.

Joan Massague et al.; "Stimulation by Insulin-Like Growth Factors is Required for Cellular Transformation by Type Transforming Growth Factor"; The Journal of Biological Chem.; Apr. 25, 1985, 260(8), 4551-4.

Hideji Nakamura et al.; "Molecular Cloning of Complementary DNA for a Novel Human Hepatoma-Derived Growth Factor"; The Journal of Biological Chemistry; Oct. 7, 1994; pp. 25143-25149; vol. 269; No. 40.

Wolfram Haupt et al.; Post-Transcriptional Inhibition of Glutamine Synthetase Induction in Rat Liver Epithelial Cells Exerted by Conditioned Medium from Rat Hepatocytes; Life Sciences; 2000, vol. 67, pp. 3191-3198.

* cited by examiner

CONDITIONED CELL CULTURE MEDIUM, METHOD TO OBTAIN THE SAME AND USE OF IT FOR MAINTENANCE, PROLIFERATION AND DIFFERENTIATION OF MAMMALIAN CELLS

FIELD OF THE INVENTION

The present invention relates to a conditioned cell culture medium and a corresponding method to obtain it. The invention also refers to methods of using this cell-conditioned medium for the maintenance, proliferation and differentiation of mammalian cells. The culture medium produced in accordance with the present invention is conditioned by the cell secretion activity of murine cells, in particular, those differentiated and immortalized transgenic hepatocytes, named MMH (Met Murine Hepatocyte). These media are employed in in vitro cell culture systems to induce maintenance, proliferation and differentiation of mammalian cells. The cells named MMH are differentiated non transformed murine hepatocytes that produce important biological molecules (e.g cytokines and growth factors) and, in accordance with the present invention, they are used in in vitro cell culture systems for the maintenance, proliferation and differentiation of mammalian cells.

BACKGROUND ART

The great expectance aroused in the past few years for the so called cellular therapy and gene therapy is limited by current methods for the cultivation of specific cell types in vitro.

New methods for the maintenance, survival, proliferation and differentiation of the different cell populations are needed.

Generally, methods for cell culture make use of culture media supplemented with growth factors and cytokines which exert specific biological effects on cells. The cell culture medium may be any cell culture medium which adequately addresses the nutritional needs of the cells being cultured.

Cytokines and growth factors are involved in a number of critical cellular processes including proliferation, adhesion, morphologic appearance, differentiation, migration, inflammatory responses, angiogenesis, and death. A list of soluble factors currently used for cell cultivation includes, but is not limited to, the following growth factors and cytokines: EGF, HGF, IGFII, TGFbeta, FGF, VEGF, PDGF, IL-3, IL-6, G-CSF, GM-CSF, SCF, IL-15, IL-11, NGF, erythropoietin etc.).

Alternatively, in order to favour the cultivation of precursor cells, and in particular for those of hematopoietic origin, stromal cells lines are used as feeder cells (Kittler E L et al. Blood. 1992; 22:3168-3178. Eaves C J. et al. Blood. 1991; 78:110-117. Krebsbach P H. et al. Crit Rev Oral Biol Med. 1999; 10:165-181; Charbord P. et al. Exp Hematol. 2002; 30:1202-1210).

The above mentioned methods of cultivation have several drawbacks.

Culture media supplementation with specific soluble factor cocktails, that appears an absolute requirement for the maintenance and/or differentiation towards specific differentiate programs of stem cells is expensive.

The major drawback of cultures utilizing feeder cells is the difficulty of procedures for the separation of the generated cells from the feeder cell. Indeed, the generated cells may be partially adherent to the feeder cells and the manual separation of the two cellular types results in an extremely hard-work. Moreover, the yield of recovered cells is often affected.

In order to solve these problems, the use of some media conditioned by different cell types has been proposed. When incubated with specific cell types, the culture medium becomes to those skilled in the art as "conditioned medium". Conditioned media contain many of the original components of the medium, as well as a variety of cellular metabolites and secreted proteins including, for example, biologically active growth factors, inflammatory mediators and other extracellular proteins specifically released by the "conditioning cells". The exact composition and therefore biological properties of each conditioned medium strictly depends on the conditioning cells.

The present invention relates to the preparation and use of a medium/conditioned by MMH cells.

The MMH cells have been described for their phenotypic and functional characteristics in several publications (Amicone L. et al EMBO J. 1997; 16:495-503. Spagnoli F M. et al. J Cell Biol. 1998; 143:1101-1112. Bellovino D. et al. J Cell Physiol. 1999; 181:24-32. Spagnoli F M. et al. J Cell Sci. 2000; 113:3639-3647. Napolitano M. et al. Free Radic Biol Med. 2001; 30:506-515. Pasquetto V. et al. J Virol. 2002; 76:5646-5653.).

It is known from Aiuti A. et al., Hepatology. 28:1645-1654 (1998) that MMH cells may be used in a cell-cell contact co-culture system with liver cells derived from 15 days postcoitum mouse embryos. It has been shown that MMH cells are able to sustain maintenance, proliferation and differentiation of hematopoietic embryonic cells; the direct contact between hepatocytes and hematopoietic cells constitutes therefore a specific culture requirement in that the cells need to be made to grow in contact with the MMH cells. Yet the co-culture has drawbacks in the analysis and use of cells so generated since this procedure requires, after the growing step, a further separation step from MMH cells. Since the hematopoietic cells partially adhere to MMH cells, the separation of the two cellular types results, as described above, in an extremely hard-work, and an inefficient number of the hematopoietic cells recovered. Moreover, the use of embryonic cells highly limits the realization of the method because of bioethics problems and difficulties in material availability.

It is known from Penington G D (Blood Cells. 1979. 5:13-23) that it is possible to cultivate bone marrow cells in a medium conditioned by hepatocytes. It is shown that the rat liver cell line BRL-3A is able to sustain the growth of megakaryocyte colonies. However this method has several drawbacks, in that BRL-3 cells have been demonstrated not to be fully differentiated hepatocytes, as revealed by the morphology of the cells and, mainly, by the lack of expression of many liver-specific genes, fundamental to retain the complex hepatic functions in vitro (Boess F et al. Toxicol Sci. 2003. 73:386-402). In addition, BRL-3A-conditioned medium has been shown to induce transformation of some mammalian cells (Massague J et al. J Biol. Chem. 1985. 260:4551-4554).

In order to improve the quality of hepatocytic conditioned media other researcher used different sources of conditioning cells. Hepatoma cells have been used (Nakamura H et al. J Biol. Chem. 1994. 269:25143-25149) but they are transformed cells. Moreover, these cells are not able to sustain the survival and/or the differentiation of mammalian cells. Allen K J et al. (J Gastroenterol Hepatol. 2000. 15:1325-32) generated conditionally immortalized mouse hepatocytes using a simian virus 40 (SV40) large T antigen (TAg) gene. SV40 in humans is associated with inflammatory kidney diseases and with specific tumor types: mesothelioma, lymphoma, brain, and bone. These human tumors correspond to the neoplasms that are induced by SV40 experimental inoculation in rodents and by generation of transgenic mice with the SV40 early region gene directed by its own early promoter-enhancer (for a recent review see Barbanti-Brodano G. Virology. 2004. 318:1-9). So these immortilised hepatocyte are potentially oncogenic transformant and for these reasons they are not suitable for the culture of cells. Other media conditioned by primary hepatocytes isolated from adult rats are described in Krause P et al. (J Hepatol. 2000. 32:718-726) Haupt W et al. (Life Sci. 2000. 67:3191-3198). However such media have several drawbacks: i) primary hepatocytes survive only few days in culture; ii) normal hepatic gene expression is down-regulated in primary hepatocytes iii) in order to produce the hepatocytes-conditioned medium at industrial scale too many animals are required to be sacrificed; iv) the isolation of primary hepatocytes from the liver is an hard work and is time and costs consuming.

SUMMARY OF THE INVENTION

It has now been found and it is an object of the present invention a culture medium conditioned by cytokines and soluble factors released by immortalized untransformed hepatocytes, said medium being characterized in that it is free from conditioning cells when used for maintenance, proliferation and differentiation of mammalian cells, including human cells.

The medium in accordance with the present invention is conditioned from the secretive activity of murine cells and in particular from differentiated and immortalized transgenic murine hepatocytes, named MMH.

Another object of the invention is the use of this conditioned medium in cellular culture systems finalized to the maintenance, expansion and differentiation of mammalian cells, in particular stem cells.

Further objects will result evident from the detailed description of the invention.

DETAILED DESCRIPTION OF THE INVENTION

Figure 1:
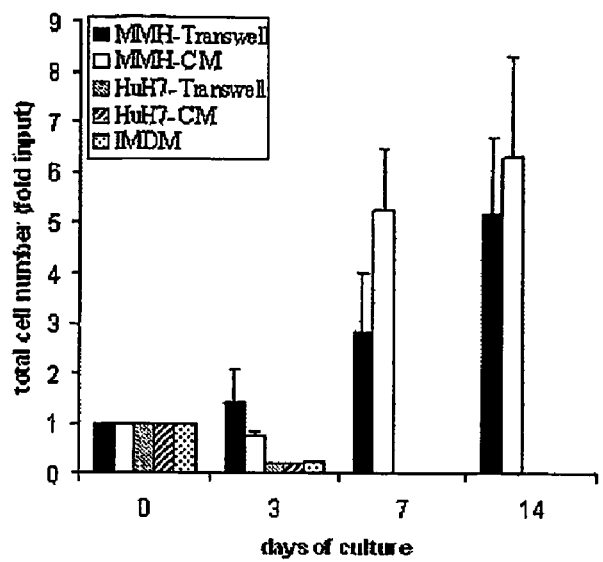
FIG. 1. Expansion of bone marrow-derived hematopoietic cells in MMH-conditioned medium culture. BM cells cultured as indicated in the inset were counted at the indicated times. Results are shown as the mean±SD of the ratio [number of cells counted after culture/number of seeded cells] (n=4).

The present invention relates to the production of a culture medium containing growth factors, cytokines and other soluble factors able to influence the survival, proliferation and differentiation of cells in culture. The cell conditioning the medium is an immortalized, cell line, characterized to be an untransformed hepatocyte, in particular MMH cells. Such cells grow in culture either in suspension or in adherence to extracellular matrix, as monolayers or three-dimensionally. The nature of the substrate on which the cells are grown may be solid, such as plastic, or semisolid gels, such as collagen, gelatin or agar or other kinds of scaffolds.

In accordance with a preferred embodiment of the invention, the conditioning cells belong to the MMH murine lines, differentiated epithelial hepatocytes that are polarized, immortalized but not transformed. The generation and the characteristics of such cells are illustrated in literature as already reported in the prior art section and therefore not described here.

In accordance with a preferred embodiment of the invention, the mammalian cells can be either differentiated or undifferentiated (i.e. adult mammalian stem cells); those cells are cultivated in the conditioned medium by MMH cells for appropriate time.

The MMH conditioned medium is prepared as follows.

MMH cells are cultivated according to standard techniques known to the skilled man in the appropriate pre-conditioned medium which adequately addresses nutritional needs of both MMH and cells that will be cultured in the MMH-conditioned medium. The preconditioned cell culture medium may be any cell culture medium which adequately addresses the nutritional needs of the cells being cultured. Examples of cell media include, but are not limited to, Dulbecco's Modified Eagle's Medium (DMEM), Ham's F12, RPMI 1640, Iscove's, McCoy's and other media formulations, including those found in Methods For Preparation of Media, Supplements and Substrate For Serum-Free Animal Cell Culture Alan R. Liss, New York (1984) and Cell & Tissue Culture: Laboratory Procedures, John Wiley & Sons Ltd., Chichester, England 1996, both of which are incorporated by reference herein in their entirety. The medium may be supplemented with any components necessary to support specific cell or issue types in vitro. Furthermore, serum, such as bovine serum, which is a complex solution of albumins, globulins and growth factors, may be added if desired.

The medium is considered conditioned by MMH when the secreted proteins, such as growth factors and cytokines, have reached desirable levels. Usually such levels are reached after a minimum of 2 hours of MMH cell growth. However a time comprised from 248 hours is preferred. After this time the cells used to condition the medium are removed with standard filtration techniques. Following the removal of the conditioning cells, the medium can be used as such or, preferably, it may require further processing it. Such processing may include, but is not limited to, concentration by a water flux filtration device or by defiltration using for example the methods described in Cell & Tissue Culture: Laboratory Procedures, supra, pp 29 D:0.1-29D:0.4.

Additionally, the conditioned medium may be further processed for product isolation and purification to remove unwanted molecules. The methods used for product isolation and purification so that optimal biological activity is maintained will be readily apparent to one of ordinary skill in the art. For example, it may be desirous to purify a growth factor, regulatory factor, peptide hormone, antibody, etc. Such methods include, but are not limited to, gel chromatography (using matrices such as sephadex) ion exchange, metal chelate affinity chromatography with an insoluble matrix such as cross-linked agarose, HPLC purification and hydrophobic interaction chromatography of the conditioned media. Such techniques are described in greater detail in Cell & Tissue Culture; Laboratory Procedures, supra. Of course, depending upon the desired application of the conditioned medium, and/or products derived thereof, appropriate measures should be taken to maintain sterility. Alternatively, sterilization may be necessary and can be accomplished by methods known to one of ordinary skill in the art, such as, for example, heat and/or filter sterilization, taking care to preserve the desired biological activity.

In another embodiment, It is possible to modify the composition of the MMH conditioned medium by direct addition of specific molecules, including proteins, glycoproteins, lipoproteins, carbohydrates, lipids, glycolipids, peptides, antibodies, cytokines, hormones, or enzymes. Such MMH-conditioned medium changes (depletion or addition) may be performed also by genetic manipulation of the MMH cells.

In another embodiment, the MMH-conditioned medium could be modified to form a solid, lyophilized, powder, gel or film. The conditioned medium may be freeze-dried and it may constitute an element of a kit.

The MMH-conditioned medium may be used to maintain, expand and differentiate mammalian cells. Mammalian cells, derived from either embryos or adults, may be of endodermic, ectodermic and mesodermic origin with particular reference to the progenitor and stem cells The mammalian cells to be cultivated in MMH-conditioned medium may be grown in suspension or in adherence, i.e. as monolayers or three-dimensional. The nature of the substrate on which the cells are grown may be solid, such as plastic, or semisolid gels, such as collagen, gelatin or agar or other scaffolds, as known in the prior art.

The cells can be cultivated in MMH-conditioned medium for the appropriate time, that may vary from few days to several weeks depending on the desired application, in term of cellular maintenance, expansion and differentiation.

The mammalian cells generated in MMH-conditioned medium can be analyzed, accordingly to procedures well known to those skilled in the art such as "phenotypic analysis".

Moreover, the mammalian cells can be utilized for further studies, for in vivo applications and in particular for therapeutical protocols, accordingly to procedures known to those skilled in the art. These therapeutical protocols include gene and cellular therapy, cellular transplantation, tissue engineering and cell factory for biological molecules production.

The mammalian cells generated in MMH-conditioned medium may also release in the conditioned medium other biological molecules, which constitute a further conditioning process of the medium. This may become object of further applications including a source for the purification of molecules of therapeutical and pharmaceutical interest.

The present invention represents an advantage for several reasons. The maintenance, proliferation and differentiation of mammalian cells in MMH-conditioned medium may not require the addition of exogenous cytokines. Moreover, the invention facilitates cells manipulation for further investigations or applications because it doesn't need the presence of a feeder-layer. Therefore, treated cells can be subsequently handled by simple separation from the invented culture medium (for example by centrifugation), allowing the recovering of all generated cells. Furthermore, the absence of a feeder layer allows procedures such as filtration of the conditioned medium that ensure the elimination of possible phatogens released by conditioning cells.

Furthermore it was unexpected the result that, according to the present invention, it is possible to cultivate both stem and differentiated cells without the necessity of a direct cell-cell contact.

It was then unexpected the result that, according to the present invention, it is possible to cultivate both stem and differentiated cells without the need for further addition of growth factors and cytokines.

Moreover, it was unexpected the result that it is possible to use cells ex vivo derived from adult mammal organisms and not from embryos.

The invention will now be described on the basis of examples, without being limited to them, to illustrate the use of MMH-conditioned medium for bone marrow-derived cell expansion and adult stem cells differentiation, with reference to the figures also.

EXPERIMENTAL PART

Materials and Methods

Culture Conditions for the Production of Conditioned Media

MMH cells were grown in RPMI-1640 as previously described in the references given in background art. HuH7 cells were grown at 37° C. in 5% CO2 in DMEM supplemented with 10% FBS, 2 mM L-glutamine, 100 u/ml penicillin and 100 µg/ml streptomycin (Gibco, Carlsbad Calif.).

In order to obtain the MMH-conditioned medium (MMH-CM) and the HuH7-conditioned medium (HuH7-CM), semi-confluent (70%) cultures were washed with 1×PBS and the respective media were replaced by IMDM, supplemented with 10% FBS and antibiotics. After 48 hours, the medium was considered MMH-CM or HuH7-CM, filtered 0.2 µm and used.

Isolation and Culture Conditions of Bone Marrow Cells

Bone marrow (BM) cells were isolated from murine femurs by flushing with 1×PBS supplemented with 5% FBS, passed through a 70 µm nylon mesh, centrifuged once and plated in complete IMDM. BM cells were incubated 1 hour on culture dishes and non-adherent cells were cultured at 37° C. in 5% CO2 in presence of medium conditioned by MMH cells or HuH7 (MMH-CM and HuH7-CM, respectively) or IMDM alone. Cells were plated at a starting density of 2040× 103 cells/cm2 in a T-25 flask. Starting from Day 3, half of the medium was replaced with fresh MMH-CM, HuH7-CM or IMDM every 2 days. In order not to lose floating cells, the replaced medium was centrifuged, cells were re-suspended in fresh medium, and then added to the same culture.

For the transwell culture system (0.4-µm filter), 6-well plates were used. The lower chamber contained the semi-confluent MMH or HuH7 feeder layer. Fresh IMDM was replaced and after 48 hours 7-12×103/cm2 BM cells were added to the upper chamber. Starting from day 3 of co-culture, the medium was replaced with fresh IMDM every 2 days.

Isolation and Culture Conditions of Sca-1+Lin− and Side Population (Sp) Stem Cells For the isolation of Sca-1+Lineage− population (Sca-1+ Lin−) BM cells were incubated with PE-conjugated mAbs for Mac-1, CD45R/B220, CD11c, Gr-1, Ter-119, CD4, CD8, U5A2-13 and FITC-conjugated mAb for Sca-1, at 4° C. for 30 min. Cells were washed twice with washing medium (WM; 1×PBS, 1% BSA, 0.1% sodium-azide) and the Sca-1+Lin− population was electronically gated and sorted using a fluorescence-activated cell sorter (FACS Vantage). The purity of this population was analyzed on a FACS Calibur.

For the isolation of the "Side Population" (SP), Hoechst staining was performed as described by Goodell M A et al., J. Exp. Med. 183:1797-1806 (1996). Cells were analyzed and sorted with a MoFlo cell sorter. Purity was always >90%.

Collected cells (Sca-1+Lin− and SP) were plated at a density that ranged between 3 and 18×103/cm2.

Single Sca-1+Lin− cells were sorted into the individual wells of a 96-well, round-bottom tissue culture plate using the Clon-CytTM system of FACS Vantage.

All cultures were incubated for 14 days in MMH-CM, replacing the medium every 3 days.

Isolation and Culture of CD34+ Mononuclear Cells from Human Cord Blood

Mononuclear cells from human cord blood were isolated by centrifugation on Lympholite. CD34+ mononuclear cells were isolated by magnetic beads separation method following the manufacturer's instructions. CD34+ cells were plated onto collagen coated 24 wells plate ($3 \times 10^5$ cells/well) in MMH-conditioned medium for 3 weeks.

Flow Cytometry Analysis for Surface Antigens

Staining was carried out in 96-well U-bottom plates. Cells were washed in WM and treated with FcBlock for 5 min at 4° C. in order to block Fc receptors prior to incubation for 15 min at 4° C. with the conjugated mAbs. Cells were washed twice in WM and fixed in 1% paraformaldehyde. Flow cytometry was performed on a FACSCalibur. A total of 104 events were acquired for each sample and analyzed with the CellQuest software. Quadrants were determined with the use of appropriate isotype controls.

Monoclonal antibodies (mAbs) ant-CD45R/B220 (RA3-6B2), the anti-Mac-1 (M1/70), the anti-CD11c (HL3), anti-CD4 (H129.19), anti-CD8 (53-6.7), anti-Ter 19 (TER119), anti-Ly6G (RB6-8C5), the anti-CD133 (293C3), the anti-CD31 (WM-59) and the NK/NK-T Cell Antigen (U5A2-13) were coupled with PE. The anti-NK1.1 (PK136), anti-CD3 (17A2), the anti-Sca-1 (E13-161.7), the anti-CD34 (AC136), the anti-CD144 (AHP628F) and the F4/80 were coupled with FITC. The PanNK (DX5) and the anti-CD45 (30-F11) were coupled with APC and PE-Cy5, respectively. The biotinylated antibody against MHC II (AF6) was coupled with Streptavidin Cy5 conjugate.

Example 1

Expansion and Differentiation of Murine Bone Marrow Hematopoietic Cells in Culture with MMH-conditioned Medium Bone marrow (BM) cells were cultured in MMH-conditioned medium for 14 days to a density between 20 and $40 \times 10^3/cm^2$ in a 25 cm² flask. Every two days half of the MMH-conditioned medium was substituted with fresh medium. At different culture times, the cells are picked and counted evaluating, then, their expansion in comparison with the number of cells at the beginning of culture.

In FIG. 1 are reported the results of bone marrow hematopoietic cells cultured in MMH-conditioned medium. The results are compared with the culture of the same cells in simple medium (IMDM), in medium conditioned by either hepatoma or MMH cell lines (HuH7-CM or MMH-CM, respectively) HuH7-Transwell in the presence or in absence of a semipermeable membrane respectively) or in co-culture with either hepatoma or MMH cell lines in the presence or in absence of a semipermeable membrane (HuH7-Transwell MMH-Transwell, respectively); the membrane prevents the direct contact between the two cellular types and allows only the passage of soluble factors.

As shown in FIG. 1, after two weeks hematopoietic cells underwent an expansion of respectively 5±1-times in co-culture with MMH, and of 6±2-times in MMH-conditioned medium. Differently, in the other control culture conditions, hematopoietic bone marrow cells rapidly die.

In order to characterize the BM cells sub-population undergoing expansion, the phenotype of cells resulting from the culture in MMH-conditioned medium was analyzed by FACS.

Table 1 compares the percentage of the positive cells for markers preferentially expressed on T cells (CD3), B cells (B220), NK cells (NK1.1) dendritic cells (CD11c), myeloid cells (Mac-1), macrophages (F4/80) and erythrocytes (Ter-119) at the moment of the isolation (day 0 of culture) with the percentage of positive cells for the same markers after 14 days of treatment in MMH conditioned medium. As shown in the table, after this time the greatest part of the cells results positive to markers associated to a NK phenotype (75±12), moreover a discrete percentage of dendritic cells (13±5) is found.

TABLE 1

Phenotypic characterization of bone marrow cells in MMH conditioned medium

| Cell Population (phenotype) | t = 0 (%) | t = 14 (%) |
|---|---|---|
| Leukocytes (CD45+) | ≧85 | 95 ± 3 |
| T cells (CD3+) | 5 ± 1 | <1 |
| B cells (B220+) | 19 ± 8 | <1 |
| Macrophages (F4/80+) | ND | <1 |
| Erythrocytes (Ter-119+) | 12 ± 1 | <1 |
| Myeloid cells (Mac-1+) | 53 ± 6 | 95 ± 3 |
| Dendritic cells (CD11c+) | 1 ± 0.5 | 13 ± 5 |
| Natural killer (NK1.1+) | 4 ± 2 | 75 ± 12 |
| (MHC-II+) | 1 ± 2 | 95 ± 3 |

Example 2

MMH-conditioned Medium Promotes the NK Differentiation of Murine Hematopoietic Stem Cell Precursors The hematopoietic stem cells (Sca-1+Lin− and "Side Population") were cultured to a density between 3 and $18 \times 10^3/cm^2$ in a 24 wells plate and cultured for 14 days in MMH-conditioned medium as described in the example 1.

As shown in Table 2, after two weeks MMH-CM promoted a significant expansion of SP- and Sca-1+Lin− derived cells (>100-fold and >40-fold, respectively). A large proportion of these cells were U5A2-13+ (74% and 43% for SP- and Sca-1+Lin− derived cells, respectively; Table 2), indicating that hematopoietic progenitor cells differentiated toward NK cell phenotype when cultured in MMH-CM.

Figure 2:
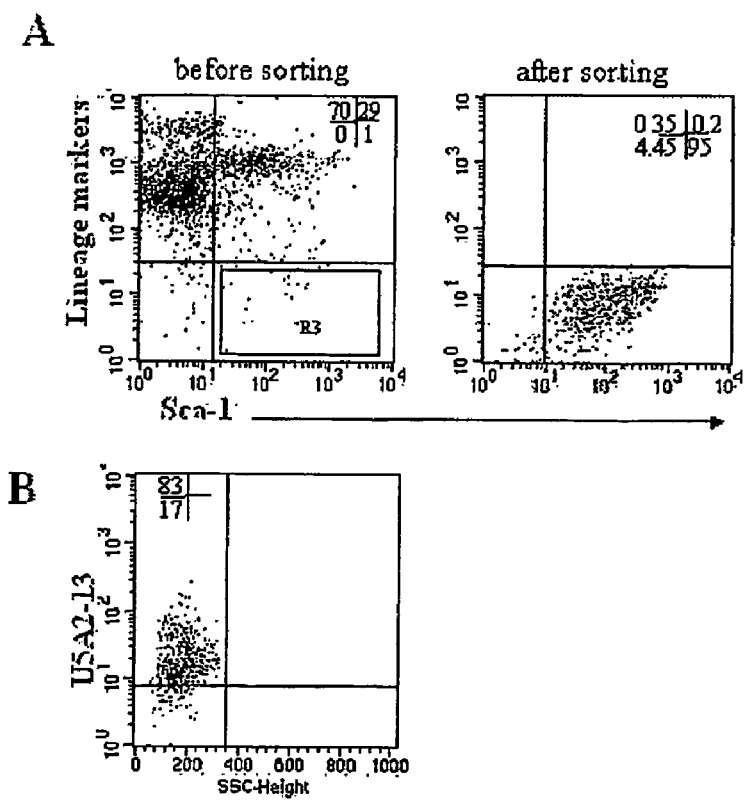
FIG. 2. MMH-conditioned medium generates U5A2-13+ NK cells from single murine Sca-1+Lin− cell. (A) Purification of BM-derived Sca-1+Lin− cells. Cells were sorted from the gate R3 shown in left panel and their purity determined by FACS re-analysis (right panel); (B) Single Sca-1+Lin− sorted cells were cultured in MMH-CM for 2 weeks. Six independent clones (average of 5000 cells each) were analyzed by FACS for the presence of U5A2-13 marker. One representative plot is shown. Percentages of each quadrant are indicated.

Moreover, single sorted Sca-1+Lin− cells were isolated, deposited by FACS into individual wells and cultured in MMH-CM. After 14 days, 27 out of the 120 single cells plated gave rise to a clone; among them six were analyzed as individual clones and found U5A2-13+ (74±10%) (FIG. 2). In view of the purity level of Sca-1+Lin− cells (>95%), 22.5% clonal efficiency obtained can not be ascribed to the proliferation of contaminating U5A2-13+ cells, but rather to the fact that the soluble factors released by MMH cells drive hematopoietic stem cell differentiation towards the NK cell lineage.

TABLE 2

MMH-CM induces NK cells differentiation from hematopoietic stem cells

| Source of hematopoietic stem cells | U5A2-13+ (% t = 14) | Fold increase of total cell numbers |
|---|---|---|
| Side Population | 74 ± 5 | 103 ± 28 |
| Sca-1 + Lin− | 43 ± 21 | 47 ± 37 |

Hematopoietic progenitor cells were stained for FACS analysis after 2 weeks of culture in MMH-CM (t=14). Results are shown as the mean number of positive cells±SD (n=3). Fold increase of MMH-CM-derived cells is reported as the mean SD of the ratio [number of cells counted after culture/ number of seeded cells].

Example 3

MMH-conditioned Medium Promotes Endothelial Cells Differentiation of Human Cord Blood Stem Cell Precursors The hematopoietic stem cells purified from human cord blood (CD34+CD133+) were cultured in a 24 wells plate ($3 \times 10^5$/well) and cultured for 3 weeks in MMH-conditioned medium. MMH-conditioned medium promoted a significant expansion of stem cells-derived cells (>8-fold). A large proportion of these cells (about 50% of stem cells-derived cells) were CD31+CD144+, resulting in a more than 30-fold increase of CD31+CD144+endothelial cells. These data indicate that hematopoietic progenitor cells from human cord blood differentiated toward endothelial cells when cultured in MMH-CM.

A sample of the MMH cells has been deposited under the Budapest Treaty at the Centro di Biotecnologie Avanzate-Interlab Cell Line Collection. The accession number for the deposit is PD09003. The date of deposit is Nov. 18, 2009. The name of the depository is Centro Di Biotechnologie Avanzate-Interlab Cell Line Collection. The address of the depository is L.go Rosanna Benzi, 10-16132 Genoa-Italy. The deposited material corresponds to the c-Met Murine Hepatocytes (MMH, clone 5/2) and whose isolation has been disclosed in a scientific publication (Amicone, et al. The EMBO Journal, 1997; 16:495-503).

The invention claimed is:

1. A method for growing, expanding, and/or maintaining isolated mammalian cells in vitro, the method comprising:
    (a) conditioning a culture medium with c-Met Transgenic Murine Hepatocyte (MMH) cells;
    (b) removing or separating the MMH cells therefrom to provide an MMH cell-free conditioned cultured medium;
    (c) contacting one or more of the isolated mammalian cells with the conditioned culture medium obtained from step (b); and
    (d) culturing the mammalian cells in the conditioned culture medium for a period of time sufficient to grow, expand, and/or maintain the mammalian cells in the contacted culture medium,
    wherein the cultured mammalian cells are selected from the group consisting of bone marrow cells, cord-blood stem cells, non-human embrional stem cells, adult stem cells, endodermal cells, ectodermal cells, mesodermal cells, natural killer (NK) cells, dendritic cells, and endothelial cells.

* * * * *

UNITED STATES PATENT AND TRADEMARK OFFICE
CERTIFICATE OF CORRECTION

| | |
|---|---|
| PATENT NO. | : 7,723,105 B2 |
| APPLICATION NO. | : 10/568194 |
| DATED | : May 25, 2010 |
| INVENTOR(S) | : Veronica Bordoni, Tonino Alonzi and Marco Tripodi |

It is certified that error appears in the above-identified patent and that said Letters Patent is hereby corrected as shown below:

Title Page, Assignee: should read

-- (73) Assignee: ISTITUTO NAZIONALE PER LE MALATTIE INFETTIVE "LAZZARO SPALLANZANI" IRCCS, Rome (IT) --

Signed and Sealed this
Fifth Day of July, 2011

David J. Kappos
*Director of the United States Patent and Trademark Office*